United States Patent [19]

Schwabe et al.

[11] Patent Number: 5,304,239
[45] Date of Patent: Apr. 19, 1994

[54] DENTAL INVESTMENT COMPOUNDS IN THE FORM OF A POWDER WITH IMPROVED FLOW PROPERTIES

[75] Inventors: Peter Schwabe, Leverkusen; Karl-Wilhelm Theis, Leichlingen; Reiner Voight, Leverkusen; Jens Winkel, Cologne, all of Fed. Rep. of Germany

[73] Assignee: Bayer Aktiengesellschaft, Leverkusen, Fed. Rep. of Germany

[21] Appl. No.: 681,239

[22] Filed: Apr. 5, 1991

[30] Foreign Application Priority Data

Apr. 12, 1990 [DE] Fed. Rep. of Germany ....... 4011871

[51] Int. Cl.$^5$ ................................................. A61K 6/00
[52] U.S. Cl. ..................................................... 106/35
[58] Field of Search ............................. 106/35; 103/35

[56] References Cited

U.S. PATENT DOCUMENTS 4,695,322  9/1987  Schwabe et al. ....................... 106/35
4,909,847  3/1990  Ohi et al. .......................... 106/38.35

FOREIGN PATENT DOCUMENTS 3707853 10/1987 Fed. Rep. of Germany ......... A61K 6/10

OTHER PUBLICATIONS

Chemical Abstracts, vol. 109, No. 20, Nov. 14, 1988 Abstract 176382j.

Primary Examiner—Paul Lieberman
Assistant Examiner—Margaret Einsmann
Attorney, Agent, or Firm—Sprung Horn Kramer & Woods

[57] ABSTRACT

In the preparation of a dental appliance wherein an investment compound is mixed with a liquid and then cast, the improvement wherein the investment compound is a plaster- or phosphate-bound investment compound which is free of an anionic surface-active agent and containing an iso-paraffin of the formula

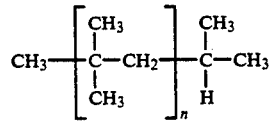

in which n denotes 2, 3, 4 or 5.

8 Claims, No Drawings

DENTAL INVESTMENT COMPOUNDS IN THE FORM OF A POWDER WITH IMPROVED FLOW PROPERTIES

The present invention relates to investment compounds based on plaster of Paris or magnesium oxide/phosphate, the preparation thereof and the use thereof for preparing cast repair materials, preferably in dentistry.

In the preparation of inlays, crowns, bridges and model cast dentures, e.g. a negative of the region of interest is prepared using impression materials and is then poured with plaster of Paris. The abovementioned restorative appliances are now modelled with wax using the plaster model. These wax models, provided with a pouring channel, are embedded in a compound consisting of a powder mixture described hereinafter and of a mixing liquid. The wax is melted or burnt out by heating, and a liquid metal alloy such as gold or chromium/cobalt alloy is introduced into the cavity which is formed. After cooling, the casting mold is destroyed and the abovementioned restorative appliances are obtained and, after further processing such as polishing, attachment of plastic or ceramic veneers, are used to close the gaps in the patient's row of teeth.

Investment compounds for preparing cast appliances in dentistry have been known for a long time. They consist of a refractory material such as quartz and/or cristobalite and of a binder such as calcium sulphate hemihydrate or magnesium oxide and ammonium dihydrogen phosphate.

These commercially available powder mixtures are, before use, mixed with mixing liquids such as water or silica sol, in a mixing ratio stated by the manufacturer, to give a pasty compound ready for use and then introduced into the casting flask with the wax model.

Another group of investment compounds consists of the refractory quartz/cristobalite in the form of a powder and of the liquid binder ethyl silicate as mixing liquid, which is likewise processed as described above.

Typical plaster-containing investment compounds contain, for example:
45–65% by weight: quartz sand
10–25% by weight: ground cristobalite
20–35% by weight: calcium sulphate hemihydrate
0–5% by weight: liquefier (for example melamine resin)
0–2% by weight: accelerator (for example potassium sulphate)
0–2% by weight: retarder (for example trisodium citrate).

Typical investment compounds containing magnesium oxide can have the following composition, for example:
40–50% by weight: quartz sand
10–20% by weight: ground quartz
15–25% by weight: ground cristobalite
6–15% by weight: magnesium oxide
6–15% by weight: ammonium dihydrogen phosphate.

The investment compounds with their properties and possible uses have been described many times, for example in Karl Eichner, Zahnärztliche Werkstoffe und ihre Verarbeitung [Dental Materials and their Processing] Volume 1, 1988, Dr. Alfred Häthig Verlag GmbH Heidelberg, pages 25–47.

DE-A 3,707,853 has disclosed dental molding compositions in the form of a powder for metal casting which display lower dust formation and which are characterized in that, besides their mixture of a soluble phosphate with a magnesium oxide or plaster hemihydrate as binder and quartz and/or cristobalite as refractory material, they have one or more liquid hydrophobic hydrocarbons, liquid hydrophobic fatty acid esters and/or liquid hydrophobic fatty acids of a vapor pressure of 4.19 mbar or below at 20° C. and additionally obligatorily contain an anionic surface-active agent which must be present as effective constituent to improve the properties. The presence of surface-active substances may, however, have adverse effects on the investment compounds.

When an investment compound in the form of a powder is mixed with the liquid component, the proportion of the liquid component should be as low as possible because a high proportion increases the setting time, reduces the compressive strength of the hardened compound and results in adhesions of the investment compound to the duplicating gel based on agar agar.

On the other hand, the mixed investment compound must have good flow properties so that there are no defects owing to zones free of investment compound.

Investment compounds based on calcium sulphate hemihydrate or magnesium oxide/ammonium phosphate have now been provided and are characterized in that they contain iso-paraffins of the formula

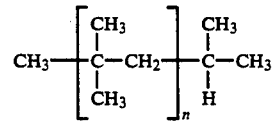

in which
n represents 2, 3, 4 or 5.

Particularly preferred iso-paraffins are those in which n represents 3 or 4.

It is, of course, possible to employ mixtures of the iso-paraffins. Particularly preferred are 2,2,4,4,6,6,8-heptamethyl-nonane and 2,2,4,4,6,6,8,8,10-nonamethyl-undecane.

The iso-paraffins have a viscosity in the range from 4 to 8 mPa.s/20° C. and a boiling point in the range from 210° to 320° C. The flashpoint is in the range from 90° to 130° C. and the ignition temperature is in the range from 375° to 420° C.

The investment compounds according to the invention preferably contain 0.5 to 5% by weight, in particular 1.5 to 3% by weight, of iso-paraffin.

The investment compounds according to the invention display improved flow properties. In addition, they are easily wetted by the mixing liquid without the presence of a surface-active agent.

In general, the plaster-bound investment compounds according to the invention contain quartz and/or cristobalite, calcium sulphate hemihydrate and additives such as boric acid, sodium chloride, potassium chloride, trisodium citrate, borax, potassium and sodium sulphate. The ethyl silicate-bound investment compounds consist essentially of quartz modifications, the binder is added before the processing as liquid ethyl silicate. The phosphate-bound investment compounds according to the invention consist of magnesium oxide and ammonium dihydrogen phosphate as binder and quartz and cristobalite as refractory material.

The investment compounds according to the invention are prepared by adding the iso-paraffin to the mixture of the abovementioned components in the form of a powder, preferably at room temperature. However, it is also possible to treat only one or some of the components with iso-paraffin and then to add the remaining components. The addition of the iso-paraffin is expediently carried out in a paddle mixer, for example a Lödige mixer, whose wall is provided with nozzles through which the iso-paraffin is sprayed onto the mixture in the form of a powder. Uniform distribution of the iso-paraffin (coating of the investment compound in the form of a powder) is optimally achieved in this way.

Apart from the improved flow properties, the investment compounds according to the invention are, surprisingly, distinguished by an improved wetting and dispersing with the mixing liquid and by a favorable mixing ratio of powder to liquid, and the expansion on setting is reduced. A reduced dust formation by the powder mixtures according to the invention has also been observed.

EXAMPLES

A phosphate-bound investment compound was prepared by mixing the following components:
Quartz sand: 45% by weight
Ground quartz: 15% by weight
Ground cristobalite: 20% by weight
Magnesium oxide: 10% by weight
Ammonium dihydrogen phosphate: 9% by weight
Coloring matter: 1% by weight The material in the form of a powder was divided into several portions which were treated in the following manner with various coating agents: The mixture was placed in a powder mixer (ploughshare mixer with 3 l volume) and sprayed from above with the particular coating agent using a spray gun. The mixer was switched off after 10 minutes.

The processing time, setting time and temperature, flow properties, compressive strength and expansion on setting were measured in accordance with DIN 13919 part 2, the mixing ratio being 100 g of investment compound in the form of a powder to 14 g of silica sol in order to obtain a pasty compound ready for use.

In addition, the samples coated in this way were tested for their relative dust formation. The apparatus used for this purpose is a chamber which has the dimensions 50×50×50 cm and which has an inlet nozzle and a suction device with a membrane filter. The pump on the suction device is switched on and adjusted to a flow rate of 27 l/min. 400 mg of sample are blown by a jet of compressed air through a sample funnel attached to the inlet nozzle into the chamber, and the pump is switched off 4 minutes later. The weight of the dust deposited on the membrane filter, multiplied by the empirical factor 9.4, yields the mean dust concentration in the chamber.

EXAMPLE 1 (comparison)

no coating agent

EXAMPLE 2 (according to the invention)

+1.5% isoeicosane (=2,2,4,4,6,6,8,8,10 nonamethylundecane)

EXAMPLE 3 (according to the invention)

+2.0% isoeicosane

EXAMPLE 4 (according to the invention)

+2.5% isoeicosane

EXAMPLE 5 (according to the invention)

+3.0% isoeicosane

EXAMPLE 6 (comparison)

+2.5% liquid paraffin oil of 180 mPa.s/23° C.+0.25% sodium lauryl sulphate

| Example | Addition | Processing time | Setting time and temperature | Measure of flow | Compressive strength 850° C. | Expansion on setting | Thermal expansion | Dust formation |
|---|---|---|---|---|---|---|---|---|
| 1 | none | 3.5 min | 6 min/75° C. | 140 mm | 20.1 N/mm$^2$ | 0.25% | 1.2% | 152 mg/m$^3$ |
| 2 | +1.5% isoeicosane | 3.75 min | 6 min/74° C. | 158 mm | 19.2 N/mm$^2$ | 0.24% | 1.2% | 103 mg/m$^3$ |
| 3 | +2.0% isoeicosane | 3.75 min | 6 min/73° C. | 153 mm | 18.0 N/mm$^2$ | 0.21% | 1.2% | 88 mg/m$^3$ |
| 4 | +2.5% isoeicosane | 3.75 min | 6 min/73° C. | 150 mm | 17.6 N/mm$^2$ | 0.19% | 1.2% | 67 mg/m$^3$ |
| 5 | +3.0% isoeicosane | 4 min | 6.25 min/72° C. | 150 mm | 15.2 N/mm$^2$ | 0.17% | 1.2% | 51 mg/m$^3$ |
| 6 | +2.5% paraffin oil +0.25% sodium lauryl sulphate | 4 min | 6.5 min/71° C. | 145 mm | 14.9 N/mm$^2$ | 0.38% | 1.0% | 69 mg/m$^3$ |

It will be understood that the specification and examples are illustrative but not limitative of the present invention and that other embodiments within the spirit and scope of the invention will suggest themselves to those skilled in the art.

What is claimed is:

1. An investment compound suitable for use in the lost wax process, which is free of an anionic surface-active agent and consists essentially of plaster or phosphate, and an iso-paraffin of the formula

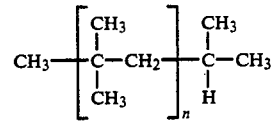

in which n denotes 2, 3, 4 or 5.

2. An investment compound according to claim 1, wherein the iso-paraffin comprises at least one of 2,2,4,4,6,6,8-heptamethyl-nonane and 2,2,4,4,6,6,8,8,10-nonamethyl-undecane.

3. An investment compound according to claim 1, containing about 0.5 to 5% by weight of the iso-paraffin.

4. An investment compound according to claim 1, containing about 1.5 to 3% by weight of the iso-paraffin.

5. An investment compound according to claim 1, containing quartz, cristobalite and calcium sulphate hemihydrate.

6. An investment compound according to claim 1, containing quartz, cristobalite, magnesium oxide and ammonium phosphate.

7. An investment compound according to claim 2, containing about 1.5 to 3% by weight of the iso-paraffin.

8. In the preparation of a dental appliance wherein an investment compound is mixed with a liquid and then cast, the improvement wherein the investment compound is a compound according to claim 1.

* * * * *